United States Patent [19]

White

[11] Patent Number: 4,719,063
[45] Date of Patent: Jan. 12, 1988

[54] METHOD OF MAKING IMPLEMENT HANDLE FOR CRIPPLED PERSONS

[75] Inventor: Robert C. White, Beamsville, Canada

[73] Assignee: Ontario Research Foundation, Mississauga, Canada

[21] Appl. No.: 795,544

[22] Filed: Nov. 6, 1985

[51] Int. Cl.$^4$ .............. B29C 39/10; B29C 67/22; B29C ; C08G 18/14; B25G 1/10

[52] U.S. Cl. .................. 264/45.2; 16/DIG. 12; 16/DIG. 19; 30/322; 30/323; 30/340; 264/46.6; 264/222; 264/271.1

[58] Field of Search .............. 264/45.2, 222, 46.6, 264/267, 314, 225, 271.1; 30/322, 323, 340; 16/DIG. 12, DIG. 19, 110 R

[56] References Cited

U.S. PATENT DOCUMENTS

| | | | |
|---|---|---|---|
| 412,479 | 10/1889 | Davis | 264/222 X |
| 1,859,317 | 5/1932 | Sponsel | 16/DIG. 12 |
| 2,205,769 | 6/1940 | Sweetland | 16/DIG. 12 |
| 2,495,119 | 1/1950 | McDevitt | 264/222 X |
| 3,048,169 | 8/1962 | Pierce | 264/222 X |
| 3,782,390 | 1/1974 | Johnson | 264/222 X |
| 4,260,574 | 4/1981 | Macomson | 264/222 X |
| 4,617,697 | 10/1986 | David | 16/DIG. 12 |
| 4,622,185 | 11/1986 | Kostich | 264/45.2 |

FOREIGN PATENT DOCUMENTS

| | | | |
|---|---|---|---|
| 656,199 | 1/1963 | Canada | 264/45.2 |
| 2250681 | 4/1974 | Fed. Rep. of Germany | 264/45.2 |
| 1000606 | 2/1952 | France | 264/222 |

Primary Examiner—Philip Anderson
Attorney, Agent, or Firm—Sims & McBurney

[57] ABSTRACT

An implement handle is made for use by a crippled person, utilizing a cap adapted to receive an end of the implement and an initially flexible bag attached to the cap. Material in the plastic state is inserted into the bag, the material becoming rigid with the passage of time, and the bag is placed into the hand of the crippled person while the material is becoming rigid. The crippled person maintain a substantially constant grip on the bag during this process, whereupon the rigidified handle conforms itself to his particular grip.

4 Claims, 5 Drawing Figures

METHOD OF MAKING IMPLEMENT HANDLE FOR CRIPPLED PERSONS

This invention relates generally to implements by crippled persons, or by persons having limited movement or flexibility in the hand.

BACKGROUND OF THIS INVENTION

It is well known that certain types of manual crippling, for example by arthritis or the like, results in an inadequate grip on certain common items like eating utensils. It would be of great use to provide a utensil which can be tailored to the particular grip capability of any given crippled person, and then to provide that person with a series of implements, all matching his or her grip.

GENERAL DESCRIPTION OF THIS INVENTION

It is accordingly the aim of an aspect of this invention to provide a method for making a handle construction which can be adapted to the particular grip of an afflicted or crippled person.

This invention provides a method of making, for use by a crippled person, a handle for an implement having an engagement end, the method comprising the steps:

(a) providing a cap adapted to receive the said engagement end, and an initially flexible bag attached to the cap, (b) inserting into the bag a material in the non-rigid state which becomes rigid with the passage of time, the material and the bag being of materials that will adhere together when the material becomes rigid, (c) placing the bag in the hand of the crippled person, and (d) having the crippled person maintain a substantially constant grip on the bag while the said material becomes rigid.

GENERAL DESCRIPTION OF THE DRAWINGS

One embodiment of this invention is illustrated in the accompanying drawings, in which like numerals denote like parts throughout the several views, and in which.

DETAILED DESCRIPTION OF THE DRAWINGS

Figure 1:
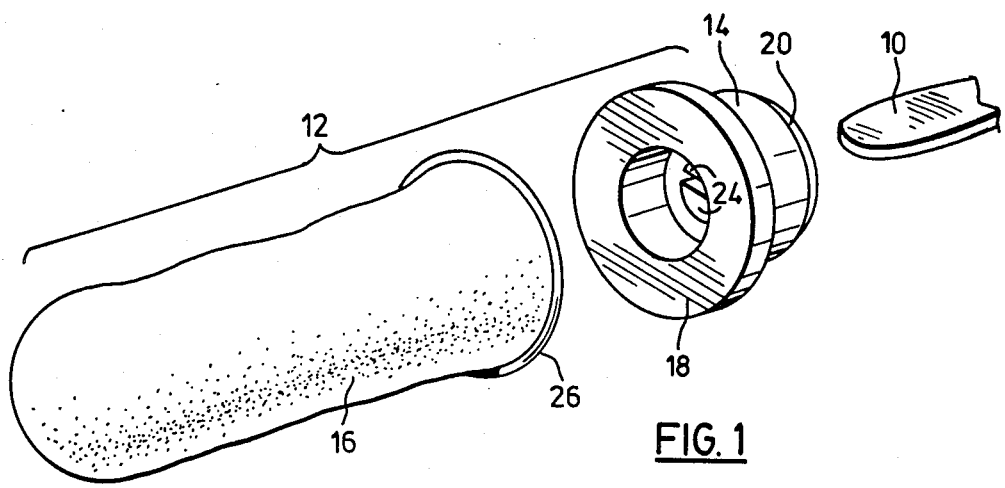
FIG. 1 is an exploded view of the main components of this invention.

Attention is first directed to FIG. 1, which shows at the upper right an engagement end 10 of an implement such as a fork, spoon, knife or the like. A handle 12 for the implement is seen to include a cap 14 which is adapted to receive the end 10, and a bag 16 intended to be attached to the cap 14.

Figures 2, 3, 4, 5:
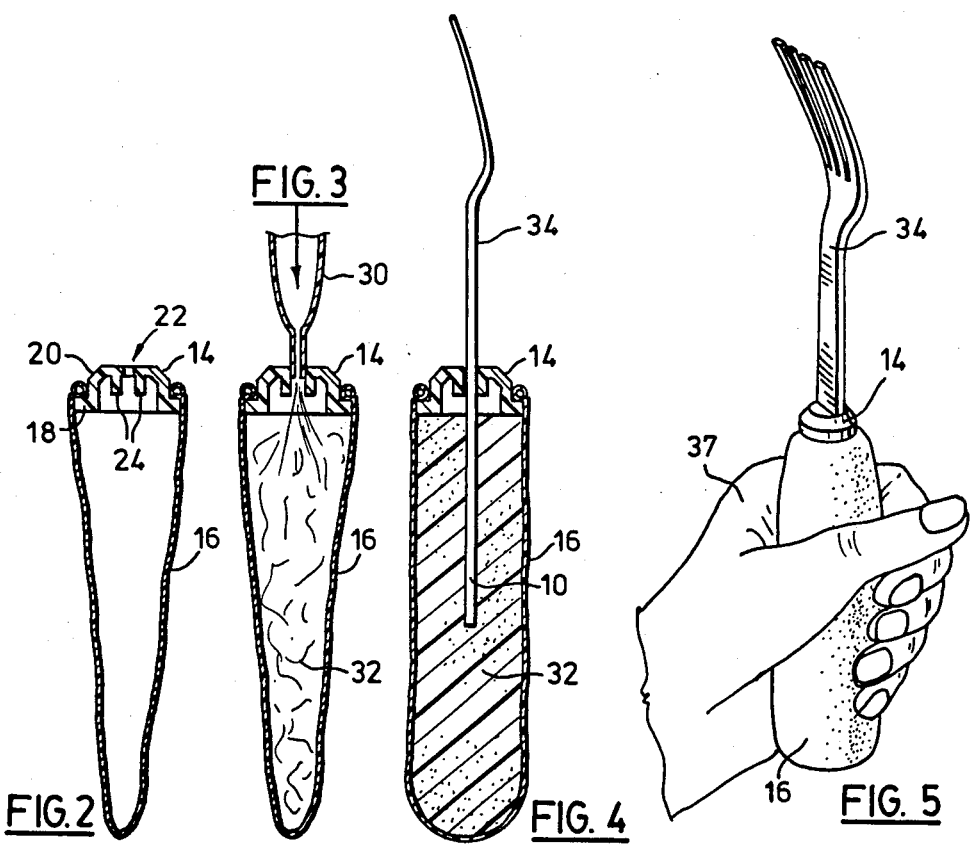
FIGS. 2, 3, 4 and 5 are sequential views, all but FIG. 5 in vertical section, showing the steps in adapting the handle to the grip of a crippled person.

As seen in FIGS. 1 and 2, the cap 14 has an annular, outwardly projecting base flange 18 and an upwardly projecting inverted cup-like portion 20. The cup-like portion 20 defines a central diametral slot 22 and incorporates two internal guiding lugs 24, one on either side of the slot 22.

The method of adapting the handle 12 to the grip of a crippled person involves several basic steps. FIG. 2 shows the cap 14 with the bag 16 engaged thereto. The bag 16 has a rolled rim 26 which is able to resiliently grip against the upper side of the flange 18.

The first step is to insert into the bag a quantity of material in the plastic state which will become rigid with the passage of time. Preferably the material is a foaming material, and one satisfactory such material is a foamable polyurethane resin. FIG. 3 shows an insertion tool 30 adapted to inject the liquid polyurethane 32 through the slot 22 of the cap 14 and into the bag 16.

The next step is to insert the engagement end 10 of an implement such as the fork 34 shown in FIG. 4, through the slot 22 of the cap 14 and into the interior of the bag 16, such that the engagement end 10 comes into contact with the foaming and rigidifying material 32.

Next, the bag is placed into the hand 37 of a crippled person, while the person maintains a substantially constant grip on the bag 16, as the material 32 completes its rigidification. After rigidification is complete, the bag will maintain its shape, which is personally tailored to the person gripping it while the foam rigidifies.

It has been found that a suitable material for the bag 16 is natural rubber latex, and that a suitable material for the cap 14 is an elastomeric solid polyurethane.

The injecting nozzle 30 is part of a conventional dual syringe dispenser of known construction, forming no part of this invention. Ideally, after the liquid polyurethane foam has been inserted into the bag, the bag is held in a vertical position and massaged in order to mix the two components together. During this time, the implement engagement end can be inserted and then after a few minutes the filled bag is placed into the patient's hand. The timing will depend on the nature of the foaming material, and the rapidity with which it sets.

It has been found that chlorination of the inner surface of the rubber bag 16 using a solution of sodium hypochlorite provides a satisfactory adhesion of the polyurethane foam to the rubber bag 16.

A satisfactory procedure for manufacturing the bag 16 is the dip moulding process, utilizing a mandrel which provides a reduced diameter neck to give a seal around the cap 14, and a somewhat tapered body to provide improved formability.

Prototype bags were manufactured using a natural rubber latex V2260 provided by General Latex, and the latex was diluted by mixing 60 parts by weight NR V2260 latex and 40 parts by weight of water. The latex was pigmented a light brown colour using Aquasperse (trade mark) tining paste manufactured by Nuodex Colortrend Limited.

The mandrel was of aluminum, and the process of manufacturing a bag involves firstly cleaning the aluminum mandrel thoroughly with water and then wiping with ethanol, following which the mandrel is dipped in a 5% calcium chloride coagulant solution and then dried for 3–5 minutes at 70° C.

The mandrel is then dipped in a dilute solution of natural rubber latex (V2260 latex) and is air dried for 1–2 minutes. The dip procedure is then repeated twice more, with air drying between dips. The bag is then oven dried at 70° C. for a few minutes, and then the latex is rolled on the neck of the mandrel to form the ring or lip 26. Oven drying for a further half hour will cure the rubber, and then talc is applied prior to peeling off the bag. The bag is then chlorinated by dipping into a 0.3% solution of sodium hypochlorite for 3–5 minutes, following which the bag is washed with a 2% aqueous ammonia solution. Washing is repeated with water, and then the bag is oven dried at 70° C. for 5-10 minutes. The bag may then be attached to the cap.

The average thickness of the bag manufactured by this process was 0.064 inches, and it was found that these bags when filled with polyurethane foam result in good formability.

For the cap 14, a suitable injection moulding process can be utilized. For the prototype cap, a two component polyurethane, Uralite (trade mark) 3142 manufactured by Hexcell Corporation, was utilized. This material has a shore hardness of 50A and reasonably good mechanical properties. It was able to accommodate various implements. Thermoplastic rubbers, however, are recommended for injection moulding in a manufacturing process, and some recommended materials are listed below:

| Thermoplastic Rubber | Shore Hardness | Supplier |
|---|---|---|
| Estane (trade mark) 58121 | 75A | B. F. Goodrich |
| Rucothane (trade mark) | 80A | Hooker, Puco Div. |
| Texin (trade mark) 480A | 86A | Mobay |
| Roylar (trade mark) E85 | 85A | Uniroyal Chemicals |

The slit 22 can be provided in the cap 14 after the cap has been moulded.

Several rigid polyurethane foams from BASF Canada were evaluated during the development stage of this device. The foams were as follows:

| Polyol | Isocynate | Density | Ratio |
|---|---|---|---|
| EXR 2076 | Isocynate 17 | 2 pcf | equal weights |
| EXR 2049 | Isocynate 17 | 10 pcf | 100 g. EXR/113 g. ISO. 17 |
| EXR 2077 | Isocynate 17 | 16 pcf | equal weights |

Of these foams, the EXR 2049/ISO 17 combination was noted to have good uniformity of surface finish, and good formability. Commercial 2049/ISO 17 has a fairly high exotherm (46° C.), however this product was compounded with reduced catalyst (0.4% Dabco 33LV per 100 pwb polyol) to provide a lower exotherm (40° C.) material suitable for this application.

The quantity of polyurethane foam required to fill the rubber bag is of course dependent upon the size of the bag. For the prototype work leading to this product, the quantity selected to sufficiently fill the bag was 10 grams of polyol and 11.3 grams of isocyanate 17, a weight ratio which corresponds to a volume ratio of 1:1, which is easily dispensed by the dual syringe dispenser.

It will be evident to those skilled in the art that other materials could be substituted for the polyurethane foams identified above, provided such substitute materials can be inserted into the bag 16 in the non-rigid state and become rigid with the passage of time.

The implement handles (engagement end 10) can be adhesively secured to the cap, if desired, in order to strengthen the implement. In the prototype development work, CS508 polyurethane adhesive can be used on the cap where it contacts the bag and the implement. Alternatively, epoxy adhesive (Mastercraft 5 minute epoxy) can be utilized. The epoxy adhesive provided a better seal between the rubber bag and cap than the polyurethane adhesive.

WASHABILITY TEST

Three implement handles were fabricated using the EXR 2049/ISO 17 polyurethane foam and sealed with the above adhesives prior to conducting the washability testing.

The washability test was carried out in a standard domestic dishwasher. After 20 cycles, the implement handle showed no degradation of the rubber, bag, cap or polyurethane foam. The seal between the bag and the cap was intact.

While one embodiment of this invention has been illustrated in the accompanying drawings and described hereinabove, it will be evident to those skilled in the art that changes and modifications may be made therein without departing from the essence of this invention, as set forth in the appended claims.

The embodiments of the invention in which an exclusive property or privilege is claimed are defined as follows:

1. A method of making, for use by a crippled person, a handle for an implement having an engagement end, the method comprising the steps:
    (a) providing a cap adapted to receive the said engagement end, and an initially flexible bag attached to the cap,
    (b) inserting into the bag a material in the non-rigid state which becomes rigid with the passage of time, the material and the bag being of materials that will adhere together when the material becomes rigid,
    (c) placing the bag in the hand of the crippled person, and
    (d) having the crippled person maintain a substantially constant grip on the bag while the said material becomes rigid.

2. The method claimed in claim 1, in which the cap has an opening for receiving said engagement end, the step (b) being carried out by injecting the material through the opening, the method further including, after step (b) and before step (c) the insertion of said engagement end through the opening and into the bag interior so that it contacts said material.

3. The method claimed in claim 2, in which the material foams as it becomes rigid.

4. The method claimed in claim 3, in which the material is a foamable polyurethane resin.

* * * * *